United States Patent [19]
Lim et al.

[11] Patent Number: 5,858,397
[45] Date of Patent: Jan. 12, 1999

[54] LIPOSOMAL FORMULATIONS OF MITOXANTRONE

[75] Inventors: Howard J. Lim; Thomas D. Madden; Marcel B. Bally; Lana W. Barber, all of Vancouver; Charmaine W. Chang, Richmond, all of Canada

[73] Assignee: University of British Columbia, Vancouver, Canada

[21] Appl. No.: 542,341

[22] Filed: Oct. 11, 1995

[51] Int. Cl.⁶ .................................................. A61K 9/127
[52] U.S. Cl. ........................................................ 424/450
[58] Field of Search ............................................ 624/650

[56] References Cited

U.S. PATENT DOCUMENTS

| | | | |
|---|---|---|---|
| 4,863,739 | 9/1989 | Perez-Soler | 424/450 |
| 4,885,172 | 12/1989 | Bally | 424/417 |
| 5,013,556 | 5/1991 | Woodle | 424/450 |
| 5,043,166 | 8/1991 | Barenholz | 424/450 |
| 5,059,421 | 10/1991 | Loughrey | 424/450 |
| 5,171,578 | 12/1992 | Bally | 424/450 |

FOREIGN PATENT DOCUMENTS

| | | | |
|---|---|---|---|
| 88/06442 | 3/1988 | WIPO | A61K 9/66 |
| 89/06977 | 2/1989 | WIPO | A61K 47/00 |
| 95/15746 | 12/1994 | WIPO | A61K 9/127 |

OTHER PUBLICATIONS

Schenkenberg, T.D., et al. (1986) "Mitoxantrone: A new anticancer drug with significant clinical activity", *Annals of Internal Medicine*, 105:67–81.

Sugarmann, S.M., et al. (1992) "Liposomes in the treatment of malignancy: a clinical perspective", *Critical Reviews in Oncology/Hematology*, 12:231–242.

Bally, M.B., et al. (1994) *Cancer Chemother. Pharamacol.*, 34:137–146.

Gabizon, A.A., et al. (1988) *Proc. Natl. Acad. Sci.*, 85:6949–6953.

Gabizon, A.A., et al. (1992) "Selective tumor localization and improved therapeutic index of anthracyclines encapsulated in long–circulating liposomes", *Cancer Res.*, 52:891–896.

Ogihara–Umeda, I., et al. (1994) "Rapid tumor imaging by active background reduction using biotin–bearing liposomes and avidin", *Cancer Res.*, 54:463–896.

Uchiyama, K., et al. (1995) "Effects of the side and fluidity of liposomes on their accumulation in tumors: A presumption of their interaction with tumors", *Intl. J. of Pharm.*, 121:195–203.

Wu, N.Z. (1993) "Increased microvascular permeability contributes to preferential accumulation of Stealth liposomes in tumor tissue", *Cancer Res.*, 53:3765–3770.

Mayer, L.D., et al. (1990) "Characterization of liposomal systems containing doxorubicin entrapped in response to pH gradients", *Biochim. Biophys Acta*, 1025:143–151.

Bally, M.B., et al. (1988) *Liposomes as Drug Carriers*, G. Gregoriadis (ed.), 841–853, John Wiler & Sons, Ltd. Chichester.

Mayer, L.D., et al. (1989) "Influence of vesicle size, lipid composition and drug to lipid ratio on the biological activity of liposomal doxorubicin in mice", *Cancer Res.* 49:5922–5930.

Boman, N.L., et al. (1993) "Optimization of the retention properties of vincristine in liposomal vincristine", *Biochim. Biophys. Acta*, 1152:253–258.

(List continued on next page.)

*Primary Examiner*—Gollamudi S. Kishore
*Attorney, Agent, or Firm*—Townsend and Townsend and Crew LLP

[57] ABSTRACT

Compositions and methods which are useful for the treatment of solid tumors in a host and which are also useful for increasing the therapeutic index of mitoxantrone in a host. The pharmaceutical compositions are liposomal formulations of mitoxantrone in which the liposomes comprise a mixture of cholesterol and a diacylphosphatidylcholine, preferably 1,2-sn-dimyristoyl-phosphatidylcholine.

10 Claims, 7 Drawing Sheets

OTHER PUBLICATIONS

Mayer, L.D., et al. (1985) "Uptake of antineoplastic agents into large unilamellar vesicles in response to a membrane potential", *Biochim. Biophys. Acta,* 816:294–302.

Parr, et al. (1994) *Biochim. Biophys. Acta,* 1195:21–30.

Madden, T.D., et al. (1990) "The accumulation of drugs within large unilamellar vesicles exhibiting a proton gradient: a survey", *Chemistry and Physics of Lipids,* 53:37–46.

Chonn, A., et al. (1991) *Biochem. Biophys. Acta,* 1070:215–222.

Weiss, R.B. (1989) "Mitoxantrone: Its development and role in clinical practice", *Oncology,* 3:135–140.

Law, S.L., et al. (1991) "Characteristics of mitoxantrone loading on liposomes", *International Journal of Pharmaceutics,* 70:1–7.

Law, S.L., et al. (1994) "Release characteristics of mitoxantrone–containing liposomes", *International Journal of Pharmaceutics,* 103:81–85.

Law, S.L., et al. (1995) "Stability of mitoxantrone–containing liposomes", *International Journal of Pharmaceutics,* 116:87–93.

Schwendener, R.A., et al. (1991) "Evaluation of incorporation characteristics of mitoxantrone into unilamellar liposomes and analysis of their pharmacokinetic properties, acute toxicity, and antitumor efficacy", *Cancer Chemother. Pharmacol.* 27:429–439.

Ehninger, G., et al. (1990) "Pharmacokinetics and metabolism of mitoxantrone", *Clin. Pharmacokinet.,* 18:365–380.

Pestalozzi, B., et al. (1992) "Phase I/II study of liposome–complexed mitoxantrone in patients with advanced breast cancer", *Annals of Oncology,* 3:445–449.

Beck, P., et al. (1993) "Influence of polybutylcyanoacrylate nanoparticles and liposomes on the efficacy and toxicity of the anticancer drug mitoxantrone in murine tumour models", *J. Microencapsulation,* 10(1):101–114.

Genne, P., et al. (1994) "Liposomal mitoxantrone for the local treatment of peritoneal carcinomatosis induced by colon cancer cells in mice", *Anti Cancer Drug Design,* 95:74–85.

Bonadonna, G., et al. (1992) "Current state of liposome––complexed drugs in the treatment of cancer patients", *Annals of Oncology,* 3:419–421.

Wolfe, J. J., et al, (1994) "Electrode potentials for bioreductive agents for neural network", *Anti–Cancer Drug Design,* 9:85–102.

LIPOSOMAL FORMULATIONS OF MITOXANTRONE

BACKGROUND OF THE INVENTION

Mitoxantrone is an anthracenedione derivative used in chemotherapy. It has demonstrated anti-tumor activity in a wide variety of experimental and human tumor models (Shenkenberg, T. D., et al., *Annals of Internal Medicine*, 105:67–81 (1986)). Phase III studies indicate activity in non-Hodgkin's lymphoma, myeloma, advanced breast cancer, bladder, ovarian and hepatocellular carcinomas in combination with other agents or as a single agent (Shenkenberg, T. D. et al., *Annals of Internal Medicine*, 105:67–81 (1986)). The toxic side effect of mitoxantrone is myelosuppression versus another related anthracycline such as doxorubicin which has a dose limiting cardiotoxicity (Saleton, S., *Cancer Treatment Reviews*, 14:297–303 (1987)). In addition to this, mitoxantrone proved to have a lower short and long term toxicity than doxorubicin. (Ehninger, G., et al., *Clin. Phamacokinet*, 18:365–380 (1990)). The precise mechanism of action for mitoxantrone is still under investigation, but it has been shown to be a DNA interchelator. As a result, it is thought that the main antitumor activity is conferred by inducing DNA strand breaks and by forming a complex with topoisomerase II (Ehninger, G., et al., *Clin. Pharmacokinet*, 18:365–380 (1990)).

It is well established in preclinical animal models that the therapeutic activity of anticancer agents can be improved through the use of liposome formulations. In general terms, liposomes engender pharmacokinetic and pharmacodistribution characteristics that give rise to increased therapeutic activity or reduced drug-related toxicity. Although the mechanism of therapeutic activity for liposomal anticancer agents is not well understood, studies have suggested that increased drug exposure at the site of tumor growth in an important attribute. Increases of tumor drug levels are a consequence of preferential accumulation of the liposome carrier within tumors. It is important to note that there is no evidence suggesting that the encapsulated form of the drug is therapeutically active, though it is postulated that antitumor activity is mediated by drug release from regionally localized liposomes.

The emphasis of investigators developing liposomal anticancer agents has, for the reasons cited above, been on using liposomal lipid compositions that: i) are less permeable to the encapsulated agent and ii) exhibit increased circulation lifetimes. Liposomes that are retained in the plasma compartment for extended periods exhibit a greater tendency to accumulate in regions of tumor growth. However, the kinetics of this extravasation process, where liposomes leave the blood compartment and enter an extravascular site, is slow. For this reason, efficient drug delivery can only be achieved with liposomes that effectively retain the drug.

Studies with liposomal formulation of the anthracycline doxorubicin suggest that properties which promote efficient delivery of drug to tumors also compromise therapeutic activity. A balance between doxorubicin retention (to maximize drug accumulation in a site of tumor growth) and release (to effect therapy) has not been achieved. Additionally, liposomal formulation of doxorubicin that release the drug following intravenous administration exhibited enhanced toxicity and increased doxorubicin accumulation in cardiac tissue.

What is needed in the art are new liposomal formulations of chemotherapeutic agents which do not suffer the drawbacks noted above. Surprisingly, the present invention provides such compositions.

SUMMARY OF THE INVENTION

The present invention provides compositions and methods which are useful for the treatment of solid tumors in a host and which are also useful for increasing the therapeutic index of mitoxantrone in a host. The pharmaceutical compositions are liposomal formulations of mitoxantrone in which the liposomes comprise a mixture of cholesterol and a diacylphosphatidylcholine, preferably 1,2-sn-dimyristoyl-phosphatidylcholine.

BRIEF DESCRIPTION OF THE DRAWINGS

FIG. 7A shows the difference in drug levels in CD1 mice. FIG. 7B shows the difference in mean survival times of BDF1 mice with a L1210 tumor burden. The dose for both experiments was 10 mg/kg.

DETAILED DESCRIPTION OF THE INVENTION

Abbreviations and Definitions

Figure 1:
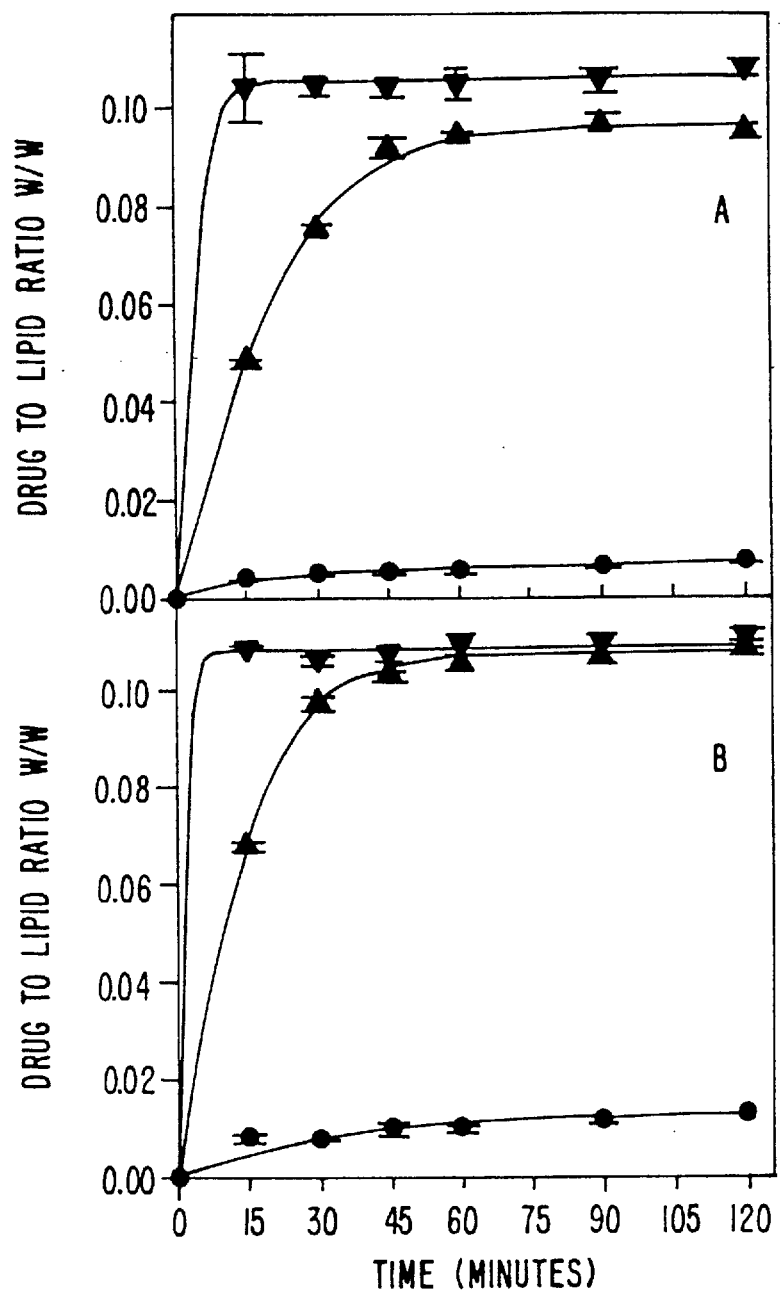
FIG. 1 shows the effect of temperature on the pH gradient loading of mitoxantrone into DSPC/Chol (A) and DMPC/Chol (B) liposomes: 37° C. (●); 50° C. (▲); 65° C. (▼).

Abbreviations used herein have the following meanings: Chol, cholesterol; DMPC, 1,2-sn-dimyristoylphosphatidylcholine; DSPC, 1,2-sn-distearoylphosphatidylcholine; EDTA, ethylenediaminetetraacetic acid; ILS, increase in life-span; HEPES, N-(2-hydroxyethyl)piperidine-N'-2-ethanesulphonic acid; HBS, HEPES buffered saline; MLV, multilammelar vesicles; PEG-DSPE, poly(ethylene glycol)-modified distearoylphosphatidylethanolamine; RES, reticulo-endothelial system; LUV, large unilamellar vesicles; PEG, poly(ethylene glycol); $^3$H-CDE, $^3$H-Cholesteryl hexadecyl ether.

As used herein, the term "mitoxantrone" refers to the free base as well as any pharmaceutically acceptable salts thereof.

Description of the Embodiments

The therapeutic index of most anticancer drugs is narrow, with severe toxic side effects occurring within the same dose range required to mediate effective therapy. A variety of experimental strategies have been developed in order to improve the therapeutic index of anticancer drugs. These strategies have a common aim: to improve drug specificity. The principal benefit postulated for use of liposomes as carriers of anticancer drugs is liposome mediated increases in drug delivery to the disease site and decreases in drug delivery to sites of target organ toxicity (Sugarmann, S. M., et al., *Critical Reviews in Oncology/Hematology,* 12:231–242 (1992)). As a result, it is important to design liposomes that (i) have a greater propensity to accumulate within disease sites (Bally, M. B., et al., *Cancer Chemother. Pharamacol.,* 34:137–146 (1994); Gabizon, A., et al., *Proc. Natl. Acad. Sci.,* 85:6949–6953 (1988); Gabizon, A. A., *Cancer Res.,* 52:891–896 (1992); Ogihara-Umeda, I., et al., *Cancer Res.,* 54:463–467 (1994); Uchiyama, K., et al., *Intl. J. of Pharm.,* 121:195–203 (1995); Wu, N. Z., *Cancer Res.,* 53:3765–3770 (1993)); (ii) have been optimized with respect to maximizing the amount of drug contained per liposome (Mayer, L. D., et al., *Biochim. Biophys. Acta,* 1025:143–151 (1990); Bally, M. B., et al., *Liposomes as Drug Carriers,* G. Gregoriadis (ed.), pp. 841–853, John Wilery and Sons, Ltd., Chichester (1988)); (iii) increase drug retention characteristics (Mayer, L. D., et al., *Cancer Res.,* 49:5922–5930 (1989); Boman, N. L., et al., *Biochim. Biophys. Acta,* 1152:253–258 (1993)) and (iv) augment the circulation lifetime of the drug loaded carrier (Gabizon, A., et al., *Proc. Natl. Acad. Sci.,* 85:6949–6953 (1988); Gabizon, A. A., *Cancer Res.,* 52:891–896 (1992)). The dilemma associated with this reasoning, however, concerns the assumption and evidence that the therapeutically active component of a liposomal anticancer drug formulation is free drug. The present invention provides compositions which establish a balance between maximizing liposome delivery to the disease site and which exhibit controlled drug release characteristics. Controlled drug release can be achieved for certain drugs by relatively simple changes in liposomal lipid composition (Boman, N. L., et al., *Biochim. Biophys. Acta,* 1152:253–258 (1993)). As demonstrated herein, using the anticancer drug mitoxantrone, controlled drug release can engender significant improvements in therapeutic activity.

Thus, in one aspect, the present invention provides a pharmaceutical composition comprising a liposomal formulation of mitoxantrone. The liposomes are prepared from a mixture of cholesterol and 1,2-sn-dimyristoylphosphatidylcholine. Preferably, the liposomes comprise of from about 50% to about 70% 1,2-sn-dimyristoylphosphatidylcholine and from about 30% to about 50% cholesterol. More preferably, the liposomes comprise about 55% 1,2-sn-dimyristoylphosphatidylcholine and about 45% cholesterol.

In one group of preferred embodiments, the pharmaceutical composition further comprises a PEG-lipid conjugate, preferably PEG-Cer-$C_{14}$, PEG-Cer-$C_{20}$ or MePEGS-2000-DSPE which is present in an amount of from about 1% to about 8% by weight.

In another group of preferred embodiments, the compositions will further comprise a targeting moiety, such as those described in co-pending U.S. Ser. No. 08/316,394, abandoned, incorporated herein by reference. Methods of attaching a targeting species such as a protein or antibody are also described therein.

For the compositions of the present invention, it was surprising that differences in drug accumulation and leakage rates for DMPC/Chol and DSPC/Chol liposomes were not detected in vitro, even when the liposomes were incubated with a serum containing buffer. The phase transition temperatures ($T_c$) for DSPC and DMPC are 55.3° C. and 23.9° C. respectively, and it was anticipated that the permeability characteristics would reflect differences in the gel to liquid crystalline phase transition of these phospholipids. Previous studies with vincristine demonstrated a good correlation between phospholipid $T_c$ and drug leakage (Boman, N. L., et al.,*Biochim. Biophys. Acta,* 1152:253–258 (1993)). It was also surprising that collapse of the transmembrane pH gradient had little impact on the drug retention characteristics for either liposomal formulation. These data contrast previous results with vincristine (Boman, N. L., et al., ibid.) and doxorubicin (Mayer, L. D., et al., *Biochim. Biophys. Acta* 857:123–126 (1986)). Moreover, it has been suggested that following pH gradient mediated uptake, drugs such as mitoxantrone, can form insoluble precipitates within the liposome (Mayer, L. D., et al., *Biochim. Biophys. Acta,* 816:294–302 (1985)). Accordingly, the permeability characteristics of the drug in a precipitated form may be less dependent on membrane characteristics or the presence of a residual transmembrane pH gradient. It is not understood, however, why differences in drug permeability become apparent in vivo.

The compositions of the present invention can be prepared by methods which are known to those of skill in the art. Typically, the liposomes are formed from the desired lipids, then loaded with mitoxantrone.

A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta,* 443:629–634 (1976); Fraley, et al., *Proc. Natl. Acad. Sci. USA,* 76:3348–3352 (1979); Hope, et al., *Biochim. Biophys. Acta,* 812:55–65 (1985); Mayer, et al., *Biochim. Biophys. Acta,* 858:161–168 (1986); Williams, et al., *Proc. Natl. Acad. Sci.,* 85:242–246 (1988), the text *Liposomes,* Marc J. Ostro, ed., Marcel Dekker, Inc., New York, 1983, Chapter 1, and Hope, et al., *Chem. Phys. Lip.* 40:89 (1986), all of which are incorporated herein by reference. Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Unilamellar vesicles are generally prepared by sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the LIPEX BIOMEMBRANE EXTRUDER®. Defined pore size in the extrusion filters may generate unilamellar liposomal vesicles of specific sizes. The liposomes may also be formed by extrusion through an asymmetric ceramic filter, such as a CERA- FLOW MICROFILTER®, commercially available from the Norton Company, Worcester Mass.

Following liposome preparation, the liposomes which have not been sized during formation may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high throughput basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.,* 10:421–450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of from about 0.05 microns to about 0.20 microns are preferred.

Methods of loading mitoxantrone or other conventional drugs into liposomes include an encapsulation technique and the transmembrane potential loading method.

In one encapsulation technique, mitoxantrone and the liposome components are dissolved in an organic solvent in which all species are miscible and concentrated to a dry film. A buffer is then added to the dried film and liposomes are formed having the drug incorporated into the vesicle walls. Alternatively, mitoxantrone can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. No. 4,885,172, U.S. Pat. No. 5,059,421, and U.S. Pat. No. 5,171,578, the contents of which are incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein(targeting species)-liposome complexes and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes having different internal and external media. Thus, for a drug which is negatively charged when ionized, a transmembrane potential is created across the membranes which has an inside potential which is positive relative to the outside potential. For a drug, such as mitoxantrone, which is positively charged in acidic media, the opposite transmembrane potential would be used.

In another aspect, the present invention provides methods of treating solid tumors in a host by administering to the host one of the above liposomal compositions of mitoxantrone. To effect delivery of mitoxantrone, the liposomes can be loaded with mitoxantrone, or optionally, mitoxantrone in combination with another therapeutic agent and administered to the subject requiring treatment. The therapeutic agents which are administered using the present invention can be any of a variety of drugs which are selected to be an appropriate treatment for the disease to be treated in the tissue. Often the drug will be an additional antineoplastic agent, such as vincristine, doxorubicin, camptothecin, cisplatin, bleomycin, cyclophosphamide, methotrexate, streptozotocin, and the like. It may also be desirable to deliver anti-infective agents to specific tissues by the present methods. The compositions of the present invention can also be used for the selective delivery of other drugs including, but not limited to local anesthetics, e.g., dibucaine and chlorpronazine; beta-adrenergic blockers, e.g., propranolol, timolol and labetolol; antihypertensive agents, e.g., clonidine and hydralazine; anti-depressants, e.g., imipramine, amitriptyline and doxepim; anti-convelsants, e.g., phenytoin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Other particular drugs which can be selectively administered by the compositions of the present invention will be well known to those of skill in the art. Additionally, two or more therapeutic agents may be administered simultaneously if desired, where such agents produce complementary or synergistic effects.

The mitoxantrone-liposome complexes of the present invention can by administered to a subject according to standard techniques. Preferably, pharmaceutical compositions of the mitoxantrone-liposome complexes are administered parenterally, i.e., intraarticularly, intravenously, subcutaneously, or intramuscularly. More preferably, the pharmaceutical compositions are administered intravenously by a bolus injection. Suitable formulations for use in the present invention are found in *Remington's Pharmaceutical Sciences,* Mack Publishing Company, Philadelphia, Pa., 17th ed. (1985).

Preferably, the pharmaceutical compositions are administered intravenously Thus, this invention provides compositions for intravenous administration which comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of mitoxantrone-liposome complexes, in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation half-lives are typically desirable for most therapeutic and diagnostic uses. One means of increasing circulation half-life is the incorporation of $GM_1$ or phospholipid-polyoxyethylene conjugates in the liposome formulation. Additionally, the phospholipid-polyoxyethylene conjugates and related lipid derivatives can be added to the compositions of the present invention as steric barrier components. The purpose of steric barrier components is to inhibit liposome—liposome interactions and thereby reduce aggregation of the liposome systems formed. Suitable steric barrier components are modified derivatives of lipids and cholesterol, such as polyethylene glycol derivatives of cholesterol (PEG-cholesterols) and PEG-lipids (e.g., phosphatidylethanolamine-polyoxyethylene conjugates and phosphatidic acid-polyoxyethylene conjugates). The polyoxyethylene conjugates which are used in the compositions of the present invention can be prepared by combining the conjugating group (i.e. phosphatidic acid or phosphatidylethanolamine) with an appropriately functionalized polyoxyethylene derivative. For example, phosphatidylethanolamine can be combined with ω-methoxypolyethyleneglycol succinate to provide a phosphatidylethanolamine-polyoxyethylene conjugate. See, Parr, et al., *Biochim. Biophys. Acta* 1195:21–30 (1994), incorporated herein by reference. Where present, the PEG-cholesterol or PEG-lipids will comprise from 0.5 to about 5.0 mole % of the total lipid composition. Other PEG-modified lipids are described in co-pending application Ser. No. 08/486,214 (e.g. MePEGS-2000-Cer). While PEG-lipid conjugates are preferred in many liposomal compositions, those compositions which are used for treatment of liver tumors will preferably not contain a PEG conjugate.

Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In yet another aspect, the present invention provides methods for increasing the therapeutic index of mitoxantrone in a patient. These methods comprise (i) encapsulating mitoxantrone in liposomes comprising a mixture of cholesterol and 1,2-sn-dimyristoylphosphatidylcholine to provide a liposomal formulation; and (ii) administering the liposomal formulation to the patient, whereby the therapeutic index of mitoxantrone is improved relative to non-liposomal formulations of mitoxantrone.

Preferred compositions and methods of administration have been discussed above.

The following examples are offered solely for the purposes of illustration, and are intended neither to limit nor to define the invention.

EXAMPLES

Materials

Novatrone (mitoxantrone hydrochloride) was obtained from the British Columbia Cancer Agency and is a product of Cyanamid (Montreal, Quebec, Canada). 1,2-sn-distearoylphosphatidylcholine (DSPC) and 1,2-sn-dimyristoylphosphatidylcholine (DMPC) were purchased from Avanti Polar Lipids (Alabaster, Alabama, USA). HEPES, citric acid, cholesterol, nigericin, and SEPHADEX® G50 (medium) was purchased from Sigma Chemical Company (St. Louis, Mo., USA). Sodium phosphate dibasic was obtained from Fisher Scientific (Fair Lawn, N.J., USA). The [$^{14}$C] mitoxantrone, used as a tracer, was generously donated by American Cyanamid. [$^3$H] Cholestesteryl hexadececyl ether, a lipid marker that is not exchanged or metabolized in vivo (Stein, Y., et al., *FEBS Lett.*, 111:104–106 (1980)), was purchased from Amersham (Oakville, Ontario, Canada). Aquacide 11 was purchased from Terochem Laboratories Ltd. (Edmonton, Alberta, Canada). Fetal bovine serum was obtained from Gibco Laboratories (Grand Island, N.Y., USA). Female CD1 and BDF1 mice were purchased from Charles River Laboratories (Ontario, Canada).

Example 1

This example illustrates the preparation of liposomal formulations of mitoxantrone.

1.1 Preparation of Liposomes

DSPC/Chol (55:45; mol:mol) and DMPC/Chol (55:45; mol:mol) liposomes were prepared, each with a small amount of [$^3$H]-cholesterol hexadecyl ether using well established extrusion technology (see Hope, et al., *Biochim. Biophys. Acta* 812:55 (1985), incorporated herein by reference). Briefly, lipid and cholesterol were dissolved in chloroform and then dried down to a homogenous lipid film under a stream of nitrogen gas. This film was then hydrated in a 300 mM citric acid buffer pH 4.0. The resulting multilamellar vesicle mixture was frozen and thawed five times before being extruded through stacked 100 nm polycarbonate filters (Nuclepore, Pleasanton, Calif.) using an extrusion device (Lipex Biomembranes Inc. Vancouver, British Columbia) as described by (Hope, M. J., et al., *Biochim. Biophys. Acta*, 812:55–65 (1985)). The large unilameller vesicles (LUV) produced were sized by quasielastic light scattering using a Nicomp 270 submicron particle sizer operating at 632.8 nm.

1.2 Encapsulation of Mitoxantrone via pH Gradient

Initial experiments were performed using mitoxantrone (with trace amounts of [$^{14}$C]-mitoxantrone) in order to determine the loading characteristics of DSPC/Chol and DMPC/Chol liposomes using the pH gradient method at various temperatures. Drug to lipid ratio was measured by applying 100 μL to SEPHADEX® G-50 mini spin columns in duplicate and spinning at 500 g for 2 minutes. Duplicate samples were taken from the resulting solution and [3H] and [$^{14}$C] were measured using a scintillation counter. Data in FIG. 1 represents the average values±SD of four measurements of the drug to lipid ratio and illustrates the temperature dependence of mitoxantrone loading via the pH gradient. At 37° C., 10% of maximum uptake is achieved after 120 minutes. As the temperature is increased to 50° C., greater than 90% of the maximum uptake occurs after 45 minutes. At 65° C., maximum uptake occurs in 15 minutes. Also illustrated in FIG. 1 is the difference in uptake due to the differences in lipid composition. The results show that at 37° C. and 65° C., there is no significant difference between the loading characteristics of the two formulations. However, at 50° C., 97% of the mitoxantrone is encapsulated within the DMPC/Chol liposomes after 30 minutes whereas only 75% of the mitoxantrone is encapsulated within the DSPC/Chol liposomes. Data for the percent of liposome loading is presented in Table 1.

TABLE 1

Comparison of Mitoxantrone Uptake by DSPC/Chol and DMPC/Chol Liposomes

| Temperature (°C.) | Time Points (minutes) | Percentage of Maximum Uptake | |
|---|---|---|---|
| | | DSPC/Chol | DMPC/Chol |
| 37 | 15 | 4.16 | 7.99 |
| | 30 | 5.09 | 7.46 |
| | 45 | 4.99 | 9.83 |
| | 60 | 5.74 | 9.72 |
| | 90 | 6.32 | 11.36 |
| | 120 | 7.43 | 12.95 |
| 50 | 15 | 46.69 | 63.13 |
| | 30 | 74.62 | 89.91 |
| | 45 | 91.60 | 96.31 |
| | 60 | 93.53 | 98.14 |
| | 90 | 96.42 | 99.37 |
| | 120 | 94.45 | 100.68 |
| 65 | 15 | 98.85 | 102.69 |
| | 30 | 98.31 | 100.15 |
| | 45 | 97.59 | 100.56 |
| | 60 | 98.38 | 103.07 |
| | 90 | 98.83 | 102.69 |
| | 120 | 100.90 | 104.28 |

Mitoxantrone was encapsulated using the transmembrane pH gradient driven loading procedure (see, Madden, et al., *Chem. Phys. Lipids* 53:37–46 (1990)). The liposomes were heated at 65° C. for 10 minutes and then added to mitoxantrone in a drug to lipid weight ratio of 0.1. Subsequently, 350 μL of 0.5M Na$_2$HPO$_4$ buffer (pH 7.5) was added to increase the pH of the mixture to between 7.0 to 7.2. The resulting solution was then incubated at 65° C. for 15 minutes. Encapsulation efficiency of mitoxantrone was determined using size exclusion chromatography on mini-spin columns made of SEPHADEX® G50 (Chonn, A., et al., *Biochem. Biophys. Acta*, 1070:215–222 (1991)). Drug and lipid concentration in the samples collected in the void volume of these columns was determined by measuring [$^3$H]-lipid and [$^{14}$C)-drug. An aliquot of the sample was mixed with Pico-Flor 40 scintillation cocktail prior to assessing radioactivity with a Packard 1900 scintillation counter.

Example 2

This example illustrates the rates of release of mitoxantrone from two liposome formulations, both in vitro and in vivo.

2.1 In Vitro Characteristics of Liposome-Encapsulated Mitoxantrone

For release studies, liposomal mitoxantrone was prepared as outlined above. The resulting drug-loaded DSPC/Chol and DMPC/Chol liposomal formulations were transferred into 25 mm diameter Spectrapor dialysis tubing (10,000–12,000 MWCO, Spectrum Medical Industries, Los Angeles), and the samples (3 mL) were dialyzed against one liter of HBS at 37° C. At the indicated time periods, 100 μL samples were taken 0, 1, 2, 4, 8, 24, 48, 72, 102 hours and assayed for drug and lipid using the mini-spin columns as described above. These studies were completed in the presence and absence of Nigericin, an ionophore that collapses the pH gradient.

Figure 2:
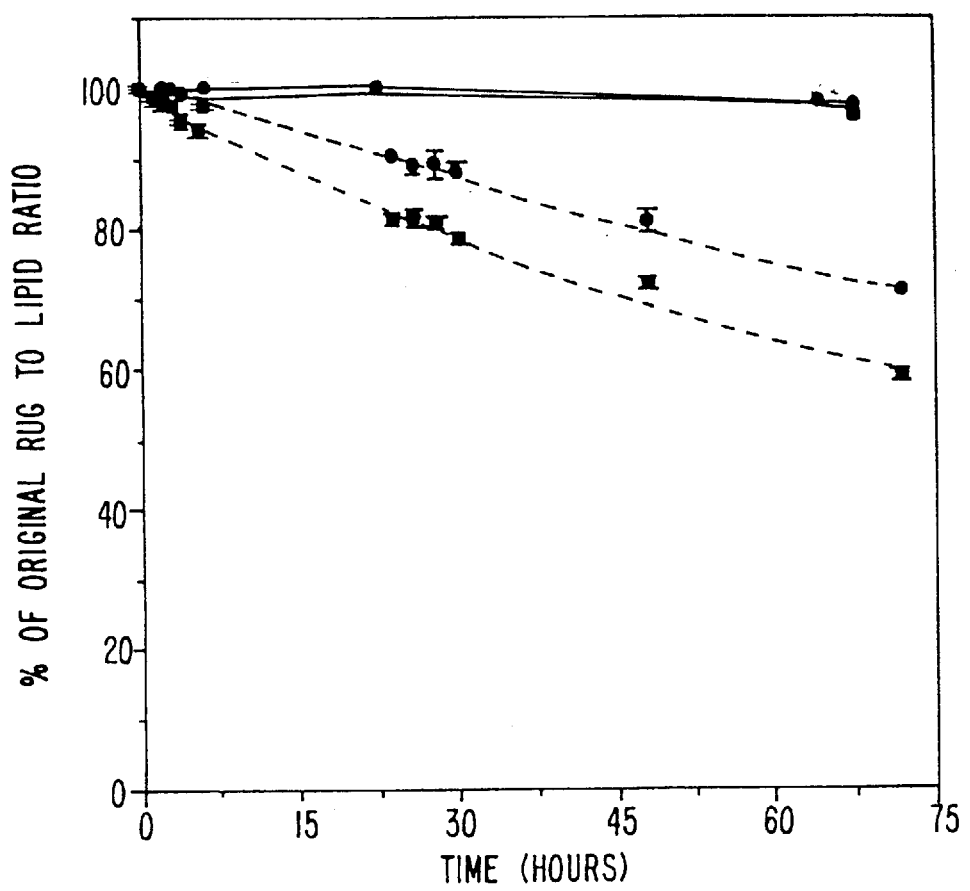
FIG. 2 shows the release of Mitoxantrone from DSPC/Chol (●) and DMPC/Chol (■) liposomes in HBS at 37° C.

FIG. 2 shows the results obtained for the release of mitoxantrone from DSPC/Chol (●) and DMPC/Chol (■) liposomes in HBS at 37° C. Solid lines indicate the absence of Nigericin. Dashed lines indicate the addition of Nigericin at time zero. Samples were taken from the dialysis bags and applied to SEPHADEX® G50 mini spin columns in duplicate and spun at 500 g for 2 minutes. Duplicate samples were taken from the resulting solution and [$^3$H] and [$^{14}$C] were measured using a scintillation counter. Data represents the average values±SD of four measurements of the drug to lipid ratio. With pH gradient intact, there is not a significant decrease in the drug to lipid ratio of both the DSPC/Chol and DMPC/Chol liposome. At 37° C., virtually all of the mitoxantrone is associated with the liposomes after 67.5 hours. However, with the addition of Nigericin, there is some release of mitoxantrone from the liposomes. As FIG. 2 demonstrates at 102 hours, 70% of the mitoxantrone is associated with the DSPC/Chol liposomes whereas 50% of the mitoxantrone is associated with DMPC/Chol liposomes.

2.2 In Vivo Release of Mitoxantrone

For plasma clearance studies, female CD1 mice (20–25 g, four per group) were injected with a 10 mg/kg drug dose i.v via the lateral tail vein. At 1, 4, 24, and 48 hours, the animals were terminated by CO$_2$ asphyxiation and whole blood was collected via cardiac puncture. The collected blood was immediately placed into EDTA coated tubes (MICROTAINERS® from Becton Dickinson). Subsequently, plasma was prepared by centrifuging the EDTA treated whole blood at 500×g for 10 min. Lipid and drug was assayed via [$^3$H]-Cholesteryl hexadecyl ether and I$^{14}$C]-mitoxantrone tracer using a scintillation counter as described above.

Figure 3:
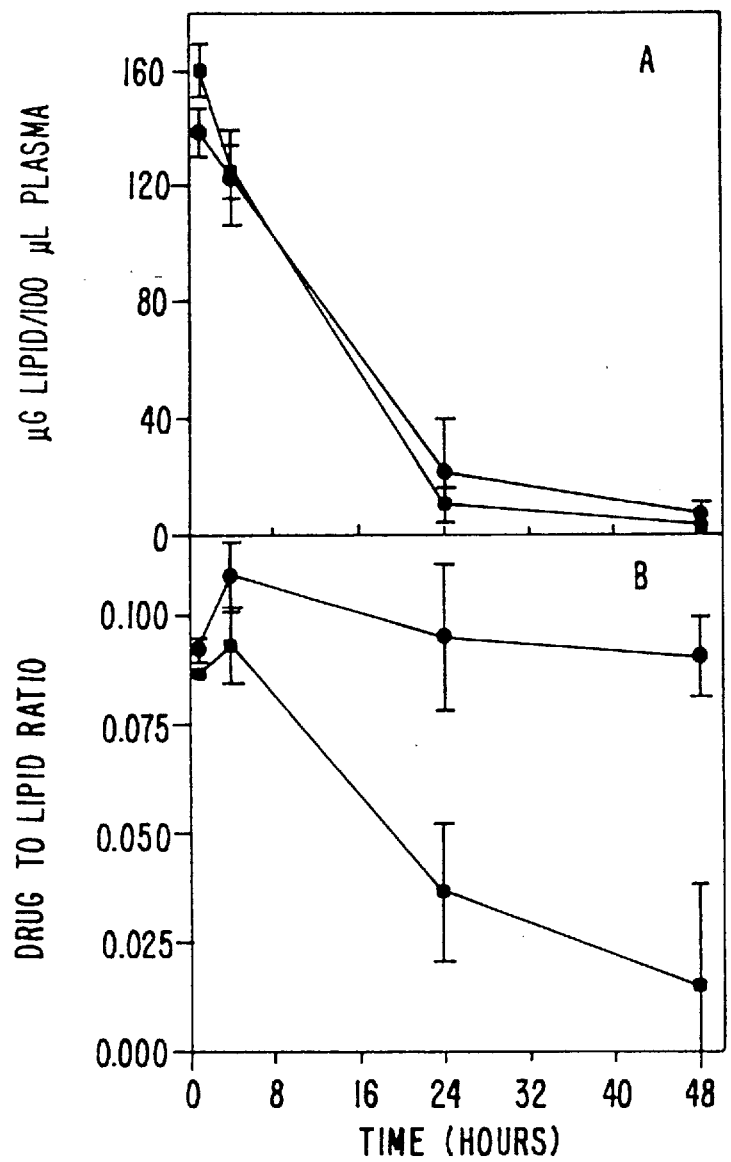
FIG. 3 shows the in vivo release of mitoxantrone from DSPC/Chol (●) and DMPC/Chol (■) liposomes.

Results shown in FIG. 3 demonstrate that plasma elimination of mitoxantrone loaded DMPC/Chol and DSPC/Chol liposomes are similar following i.v. administration in female CD1 mice (see FIG. 3A). An estimation of the amount of mitoxantrone retained in the liposomes that are in the circulation can be made by determining the ratio of mitoxantrone-to-lipid at the indicated time points. This estimation assumes that the level of free drug in the plasma of animals given liposomal mitoxantrone will be negligible. The results of such an analysis, shown in FIG. 3B, demonstrated that there is greater release of mitoxantrone from the DMPC/Chol liposomes than the DSPC/Chol liposomes. For DMPC/Chol liposomes, 73% of the mitoxantrone originally associated with the carrier has been released within 48 hr. In contrast, less than 5% of the drug was released from DSPC/Chol liposomes. Between the 4 h and 48 h time points the rate of mitoxantrone release was estimated to be 1.7 and <0.025 μg mg-lipid$^{-1}$ hr$^{-1}$ for DMPC/Chol and DSPC/Chol liposomes, respectively. These results are consistent with results obtained with doxorubicin (Mayer, L. D., et al, *J. Liposome Res.*, 4:529–553 (1994)) and clearly demonstrate that control of in vivo mitoxantrone release rates can be achieved through simple changes in liposomal lipid composition. It should be noted that plasma drug levels obtained following administration of free drug are significantly less than those obtained with the liposomal formulations. Trapezoidal area-under-the-curve (AUC) analysis of plasma drug levels indicate plasma AUCs of 0.01145, 167.8615 and 229.8615 $\mu$g mL$^{-1}$ hr$^{-1}$ following administration of free mitoxantrone, DMPC/Chol mitoxantrone and DSPC/Chol mitoxantrone, respectively.

Example 3

This example illustrates the in vivo efficacy of the liposomal-mitoxantrone compositions of the present invention.

3.1 In Vivo Efficacy of Liposome-Encapsulated Mitoxantrone

BDF1 mice were injected with 10$^4$ L1210 cells i.v. twenty four hours before injection with a single treatment of 5 mg/kg, 10 mg/kg 20 mg/kg doses of free mitoxantrone; 5 mg/kg, 10 mg/kg, 20 mg/kg doses of DMPC/Chol mitoxantrone; and 10 mg/kg and 20 mg/kg doses of DSPC/Chol mitoxantrone. Injections were administered in a volume of 200 $\mu$L. In order to achieve this volume for the 20 mg/kg dose, the stock mixture was concentrated using Aquacide II. Survival times of the mice were then monitored over a sixty day time course. Increase in life span (ILS %) was calculated as follows:

$$ILS = \frac{\text{Mean survival time of treatment group} - \text{Mean survival time of control}}{\text{Mean survival time of control}}$$

Maximum tolerated dose was determined by monitoring the weight loss of the mice over a two week period. If the mice lost greater than 30% of the original weight then the mice are terminated.

The antitumor effects of free mitoxantrone and liposomal mitoxantrone were compared using the L1210 tumor model. L1210 is a murine lymphocytic leukemia. Typically this cell line is used as ascitic tumor model; however, we have found that upon i.v. injection these cells seed in the liver and the spleen. This provides identical tumor models for the two organs.

Figure 4:
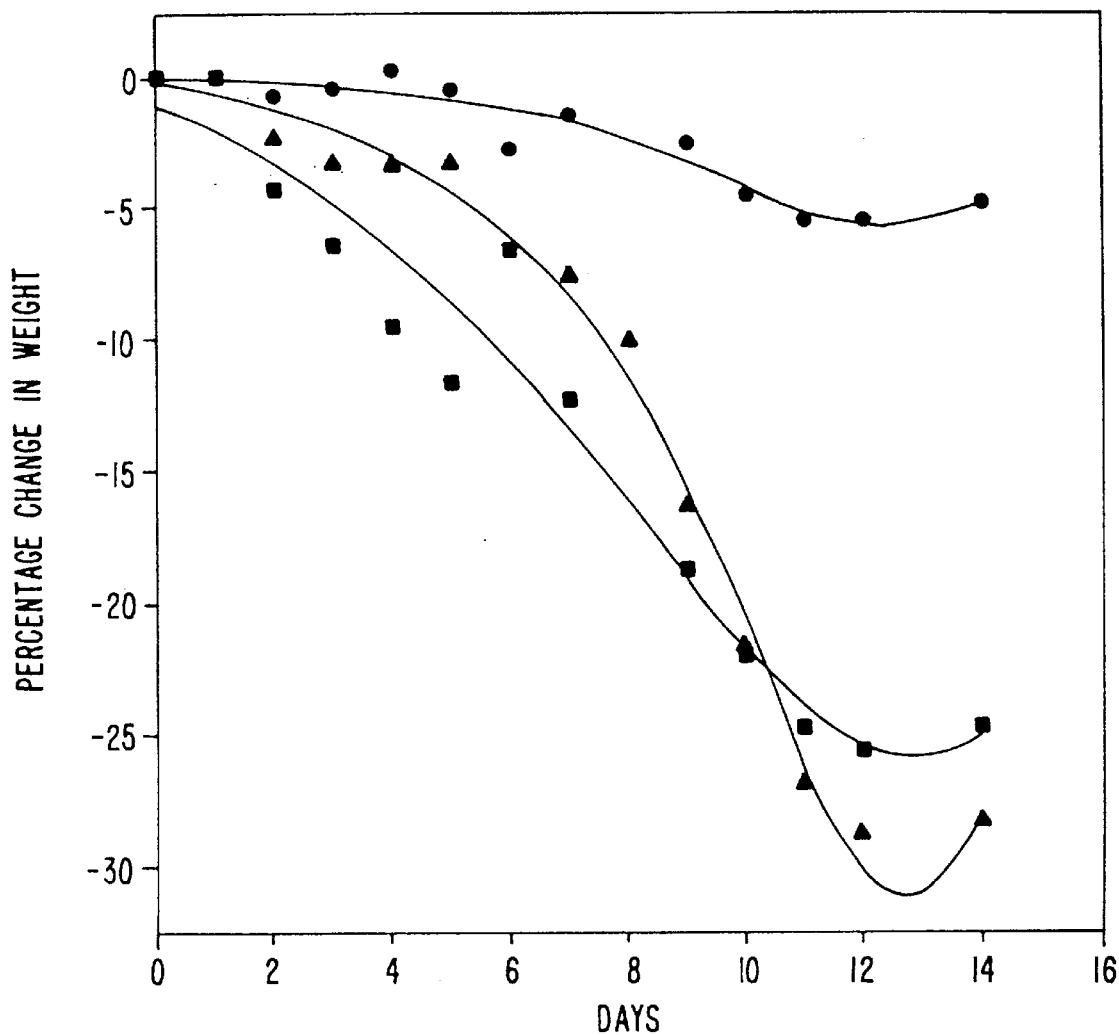
FIG. 4 shows the percentage change in body weight of BDF1 mice during efficacy studies as a means of determining maximum tolerated doses (MTD). Data shown here is the data from the determined MTD'S: DSPC/Chol at 20 mg/kg (●), DMPC/Chol at 20 mg/kg (■), and free mitoxantrone at 10 mg/kg (▲).

Toxic dose range finding studies in tumor-free female BDF1 mice found that the maximum tolerated dose (MTD) of free drug was 10 mg/kg. When the drug was encapsulated in DMPC/Chol or DSPC/Chol the MTD of mitoxantrone increased to 30 mg/kg. At this dose 100% of the animals treated survived for greater than 30 days. Necropsies suggested no gross abnormalities in any of the tissues examined. An evaluation of drug induced weight loss, however, suggested that the DMPC/Chol liposomal formulation was slightly more toxic than the DSPC/Chol system. This result was confirmed in the efficacy experiments, where changes in weight were measured over 14 days following initiation of treatment (FIG. 4). In animals that had been given (i.v) 10$^4$ L1210 cells and treated 24 h later with mitoxantrone, the maximum therapeutic dose of free and liposomal mitoxantrone was 10 and 20 mg/kg, respectively. Therefore the results in FIG. 4 show drug induced changes in weight loss at these doses. The nadir in weight loss occurred between day 12 and 13 and at this time point animals treated with free drug lost almost 30% of their original body weight. In contrast, animals treated with DMPC/Chol mitoxantrone and DSPC/Chol mitoxantrone exhibited a body weight loss of 20 and 8%, respectively.

Figure 5:
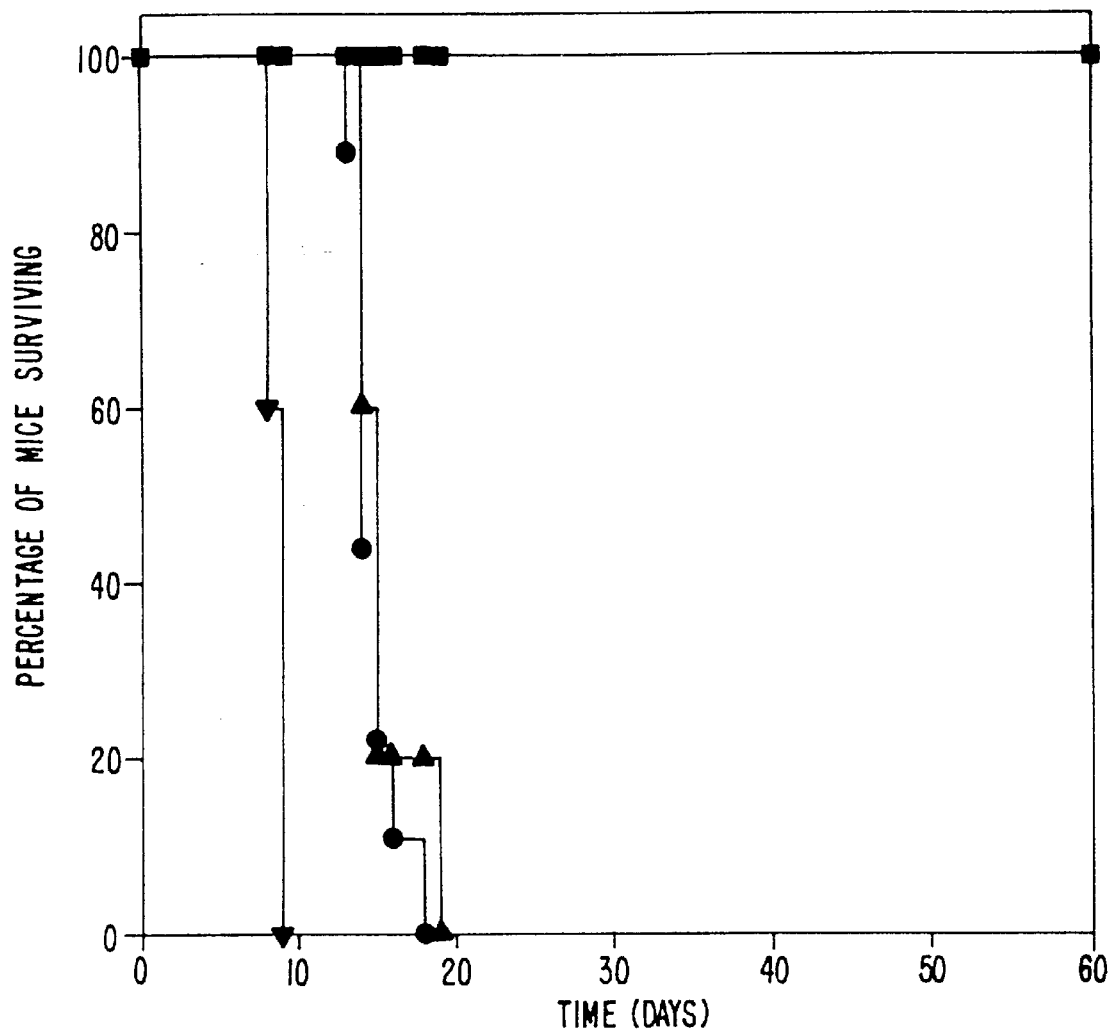
FIG. 5 shows the percentage survival of BDF1 mice injected with $10^4$ L1210 cells, i.v. via the lateral tail vein 24 hours before being treated with 10 mg/kg doses of free mitoxantrone (▲), DSPC/Chol (●), and DMPC/Chol (■) liposomal formulations. Untreated animals served as controls (▼).

The L1210 antitumor studies summarized in Table 2 and FIG. 5 clearly demonstrate that the DMPC/Chol liposomal formulation is therapeutically more active than free drug and drug encapsulated in DSPC/Chol liposomes. As shown in Table 2 the maximum % increase in life span achieved with free drug is 93%. Enhanced therapy is observed for drug encapsulated in DSPC/Chol liposomes, where a maximum %ILS value of 180 is obtained at a dose of 20 mg/kg. Improved therapy achieved with DSPC/Chol liposomal drug is primarily a consequence of liposome mediated reductions in drug toxicity. At 10 mg/kg, for example, the L1210 antitumor activity of this liposomal formulation is equivalent to free drug. Remarkably, treatment with DMPC/Chol liposomal mitoxantrone effects 100% long term (>60 day) survival even at a dose of 10 mg/kg. The survival curves obtained for animals treated at a dose of 10 mg/kg (FIG. 5) clearly show that the therapeutic activity of mitoxantrone is enhanced significantly when encapsulated in DMPC/Chol liposomes.

TABLE 2

L1210 Anti-Tumor Activity of Free and Liposomal Mitoxantrone in BDF1 Mice

| Sample | Drug Dose (mg/kg) | Lipid Dose (mg/kg) | 60 Day Survival | Mean Survival (days) | % ILS[a] | L/F[c] |
|---|---|---|---|---|---|---|
| Control | | | 0/10 | 8.6 | | |
| Free Mitoxantrone | 5 | | 0/5 | 13.6 | 58 | |
| | 10 | | 0/5 | 16.6 | 93 | |
| | 20 | | 0/5 | 12.6 | 47 | |
| DSPC/Chol | 10 | 100 | 0/10 | 14.7 | 71 | 0.89 |
| | 20 | 200 | 0/10 | 24.1 | 180 | 1.91 |
| DMPC/Chol | 5 | 50 | 0/5 | 17 | 98 | 1.25 |
| | 10 | 100 | 10/10 | >60 | ND[b] | ND |
| | 20 | 200 | 10/10 | >60 | ND | ND |

[a]Percentage ILS (Increase in Life Span) Values were determined from mean survival times of treated and untreated control groups. If the animals survived more than 60 days the ILS % was not determined.
[b]ND not determined.
[c]L/F (Liposomal/Free) values were calculated by dividing the mean survival time of the liposomal formulation by the mean survival time of the free drug at the equivalent dose.

Figure 6:
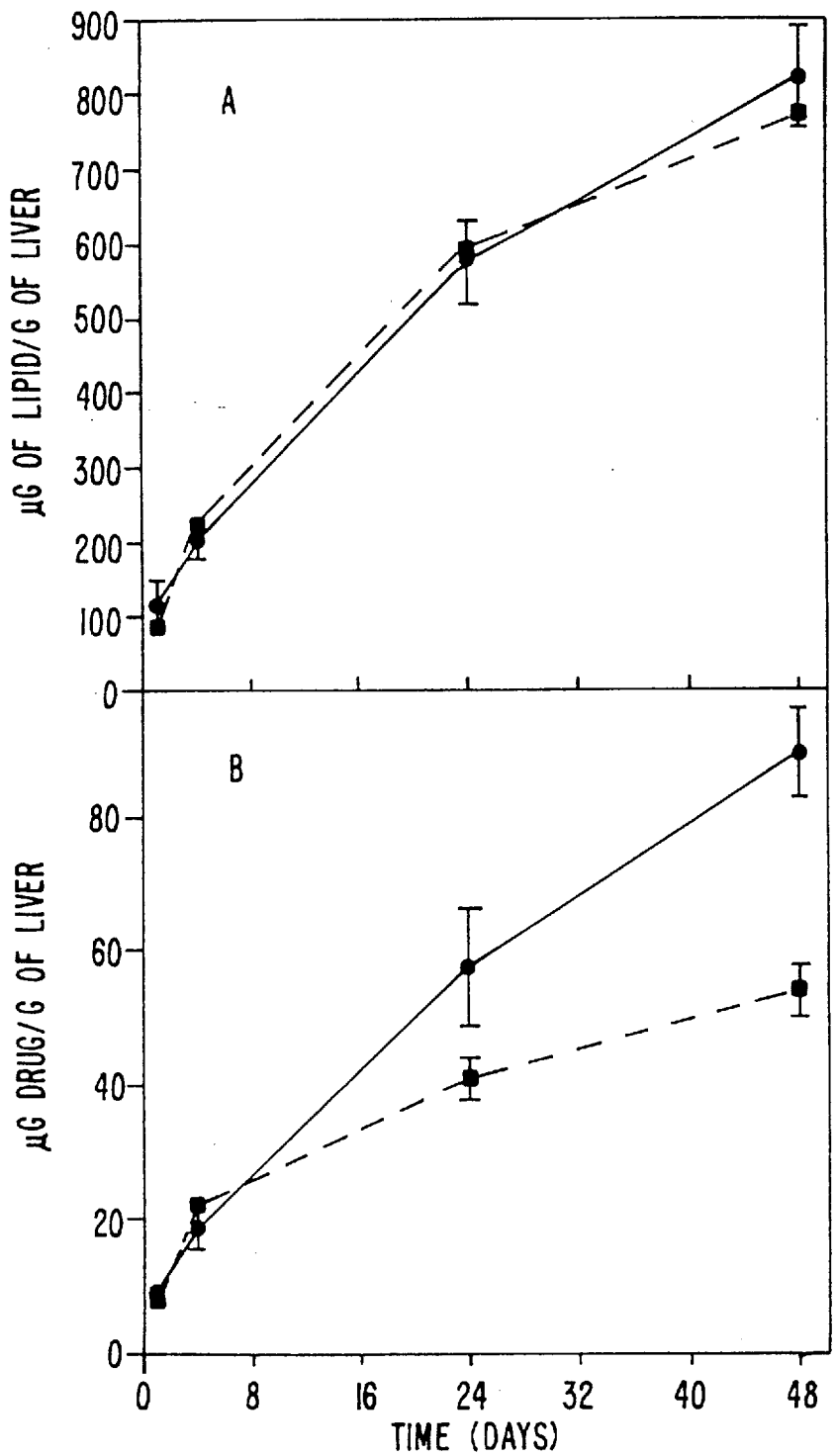
FIG. 6 shows the amount of lipid and drug which accumulate in the liver of CD1 mice over a period of 48 days for DMPC/Chol liposomal mitoxantrone (■) and for DSPC/Chol liposomal mitoxantrone (●).

The results summarized thus far demonstrate that the therapeutic index of mitoxantrone can be increased dramatically by encapsulating the drug in DMPC/Chol liposomes. The rate of drug release is at least 68-fold faster from DMPC/Chol liposomes in comparison with DSPC/Chol liposome. In addition to assessing drug release from liposomes in the plasma compartment it is important to correlate antitumor activity with drug exposure at the site of tumor growth. For this reason drug delivery to the liver, a primary site of disease progression for the tumor model employed here, was also evaluated. The results, shown in FIG. 6, were obtained in tumor-free CD1 mice, however it should be noted that drug/liposome plasma elimination and biodistribution data were similar in tumor-free CD1 and tumor-bearing (L1210 cells given 24 hr prior to drug injection) BDF1 mice. As shown in FIG. 6A liposomal lipid accumulation in the liver is similar for both DSPC/Chol and DMPC/Chol liposomal mitoxantrone formulations. Unlike doxorubicin (Mayer, L. D., et al., Cancer Res., 49:5922–5930 (1989)), the presence of entrapped mitoxantrone did effect reductions in liposomal lipid accumulation in the liver. The level of mitoxantrone achieved in the liver 24 and 48 hours after i.v. administration of DMPC/Chol liposomal mitoxantrone is, however, significantly less than that observed for DSPC/Chol mitoxantrone.

Figure 7:
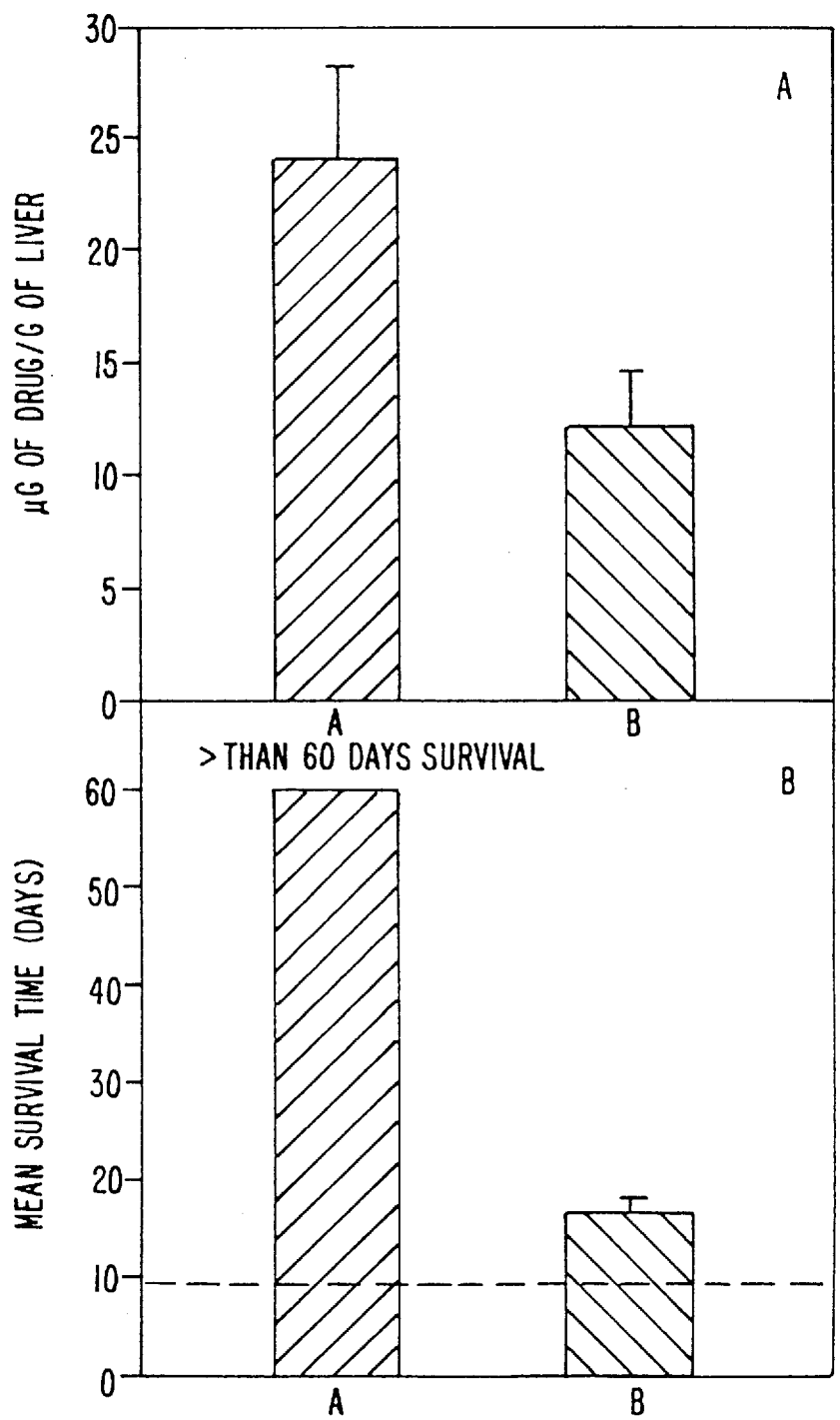
FIG. 7 shows the changes in distribution and efficacy due to incorporation of 5 mole % DSPE-PEG into the DMPC/Chol liposome formulations of mitoxantrone (A is without added DSPE-PEG and B is with the added DSPE-PEG).

The above data shows that maximizing drug delivery to the site of tumor growth is can result in little therapeutic value unless the drug can escape from the liposomal carrier. Provided that the drug is permeable across the liposome membrane, the importance of maximizing drug delivery can be established. It would, for example, be predicted that factors that reduce accumulation of DMPC/Chol liposomes in the liver would mediate reduction in i.v. L1210 antitumor activity. The results summarized in FIG. 7 clearly support this prediction. In these studies the tendency for DMPC/Chol liposomal mitoxantrone to accumulate in the liver was reduced by incorporation of 5 mole % poly(ethylene glycol)-distearoylphosphatidylethanolamine (PEG-DSPE). PEG-PE/DMPC/Chol liposomes exhibited comparable drug release characteristics in vivo (results not shown), however the amount of drug delivered to the liver was reduced by a factor of 2 (FIG. 7A). Reduction in liver accumulation was associated with increased levels of drug and lipid in the plasma compartment (results not shown). As shown in FIG. 7B there was a surprising reduction in the antitumor activity of mitoxantrone encapsulated in the PEG-PE/DMPC/Chol liposomes.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A pharmaceutical composition for the treatment of solid tumors, comprising a liposomal formulation of mitoxantrone, said liposomes consisting essentially of a mixture of about 30% to about 50% cholesterol and about 50% to about 70% 1,2-sn-dimyristoylphosphatidylcholine and said mitoxantrone being encapsulated in the aqueous interior of said liposomes.

2. A pharmaceutical composition in accordance with claim 1, further comprising a PEG-lipid conjugate.

3. A pharmaceutical composition in accordance with claim 2, wherein said PEG-lipid conjugate is selected from the group consisting of PEG-Cer-$C_{14}$, PEG-Cer-$C_{20}$ and MePEGS-2000-DSPE.

4. A pharmaceutical composition in accordance with claim 2, wherein said PEG-lipid conjugate is present in an amount of from about 1% to about 8% by weight.

5. A method of treating solid tumors in a host, said method comprising administering to said host a pharmaceutical composition in accordance with claim 1.

6. A method for increasing the therapeutic index of mitoxantrone in a patient, said method comprising, (i) encapsulating mitoxantrone in liposomes comprising a mixture of cholesterol and 1,2-sn-dimyristoylphosphatidylcholine to provide a liposomal formulation; and (ii) administering said liposomal formulation to said patient, whereby said therapeutic index of mitoxantrone is improved relative to non-liposomal formulations of mitoxantrone.

7. A method in accordance with claim 6, wherein said liposomes comprise a mixture of from about 50% to about 60% 1,2-sn-dimyristoylphosphatidylcholine and from about 40% to about 50% cholesterol.

8. A method in accordance with claim 7, wherein said mixture further comprises a PEG-lipid conjugate.

9. A method in accordance with claim 8, wherein said PEG-lipid conjugate is selected from the group consisting of PEG-Cer-$C_{14}$, PEG-Cer-$C_{20}$ and MePEGS-2000-DSPE.

10. A method in accordance with claim 8, wherein said PEG-lipid conjugate is present in an amount of from about 1% to about 8% by weight.

* * * * *